United States Patent
Schulz

[11] Patent Number: 6,051,749
[45] Date of Patent: Apr. 18, 2000

[54] FABRIC OR GARMENT CONTAINING FECAL ENZYME INHIBITOR

[75] Inventor: Anthony A. Schulz, Floyds Knobs, Ind.

[73] Assignee: Enviroderm Pharmaceuticals Inc., Louisville, Ky.

[21] Appl. No.: 08/956,457

[22] Filed: Oct. 23, 1997

Related U.S. Application Data

[62] Division of application No. 08/631,119, Apr. 12, 1996, Pat. No. 5,869,033.

[51] Int. Cl.⁷ ............................... A61F 13/00; A47K 7/03
[52] U.S. Cl. .............................................. 604/368; 424/402
[58] Field of Search ................................ 424/78.08, 402; 604/367, 368

[56] References Cited

U.S. PATENT DOCUMENTS

| | | | |
|---|---|---|---|
| 2,750,944 | 6/1956 | Tollstrup | 604/368 |
| 3,657,760 | 4/1972 | Kudisch et al. | 15/104.93 |
| 3,935,363 | 1/1976 | Burkholder | 428/281 |
| 5,665,368 | 9/1997 | Lentini et al. | 424/401 |
| 5,836,929 | 11/1998 | Bewick-Sonntag et al. | 604/368 |

FOREIGN PATENT DOCUMENTS 2649974  5/1977  Germany .

*Primary Examiner*—Peter F. Kulkosky
*Attorney, Agent, or Firm*—Vorys Sater Seymour & Pease, LLP

[57] ABSTRACT

Skin irritation, such as diaper rash, appearing when the skin is allowed to remain in contact with proteolytic enzymes found in feces is prevented by inactivating the fecal proteolytic enzymes by contact with organophilic clays. The organophilic clays are applied to the skin in areas likely to come into contact with feces or to garments such as diapers. A composition suitable for practicing the method of the invention comprises an amount of an organophilic clay effective to inactivate irritating fecal proteolytic enzymes dispersed in a pharmaceutically acceptable non-toxic dermatological vehicle. A fabric incorporating organophilic clay, preferably dispersed in a matrix of a superabsorbent polymer is useful for preparing diapers for infants that can help to prevent skin irritation by fecal enzymes.

31 Claims, No Drawings

FABRIC OR GARMENT CONTAINING FECAL ENZYME INHIBITOR

This is a divisional of application Ser. No. 08/631,119 filed on Apr. 12, 1996 now U.S. Pat. No. 5,869,033.

BACKGROUND OF THE INVENTION

1. Field of the Invention

This invention relates to methods of prevention of skin irritation such as diaper rash and more particularly to prevention and treatment of diaper rash caused by fecal enzymes.

2. Brief Description of the Prior Art

Diaper rash is a form of contact dermatitis which afflicts infants whose wet and/or soiled diapers are not promptly changed. Because of the practical impossibility of attending promptly to all of an infant's needs, even those infants receiving a high level of care sometimes suffer from diaper rash.

It has recently come to be understood that the initial stages of some types of diaper rash are the result of skin irritation caused by contact with digestive enzymes present in infant feces, particularly trypsin, chymotrypsin and elastase. These enzymes are proteolytic enzymes produced in the gastrointestinal tract to digest food. In infants, the feces tend to be watery and they contain, among other materials such as bacteria, some amounts of undegraded digestive enzymes. These enzymes, if they remain in contact with the skin for any appreciable period of time have been found to cause an irritation that is uncomfortable in itself and can predispose the skin to infection by microorganisms.

Conventional methods of preventing or alleviating diaper rash have included application of powders to keep the skin dry and creams and ointments to protect the skin from contact with irritants. However diaper rash continues to be a problem for infants and parents.

Similar conditions conducive to skin irritation by proteolytic enzymes present in feces are found in patients having colostomies and the like. Such patients also would benefit from improved treatments to prevent skin irritation due to fecal enzymes.

Accordingly, a need has continued to exist for additional methods of preventing and treating diaper rash and similar skin irritations.

SUMMARY OF THE INVENTION

The need for additional methods of preventing diaper rash has now been met by the method of this invention wherein fecal proteolytic enzymes are inactivated by contact with organophilic clays. A composition suitable for practicing the method of the invention comprises an amount of an organophilic clay effective to inactivate irritating fecal proteolytic enzymes dispersed in a pharmaceutically acceptable non-toxic dermatological vehicle.

In a further embodiment of the invention a composition containing organophilic clay, e.g, a superabsorbent polymer containing an organophilic clay, is incorporated into a fabric that is used to make garments, such as diapers, that may come into contact with feces containing skin-irritating enzymes.

Accordingly, it is an object of the invention to provide a method for preventing diaper rash.

A further object is to prevent contact dermatitis due to fecal enzymes.

A further object is to provide a composition for application to the skin that can prevent diaper rash.

A further object is to provide a composition for application to the skin that can prevent contact dermatitis due to proteolytic enzymes such as those present in feces.

A further object is to provide a method of inactivating skin-irritating fecal enzymes.

A further object is to provide a composition capable of inactivating skin-irritating fecal enzymes.

A further object is to provide a composition capable of inactivating skin-irritating fecal enzymes that can be incorporated into a fabric.

A further object is to provide a fabric incorporating a composition that is capable of inactivating skin-irritating fecal enzymes.

A further object is to provide a garment such as a diaper incorporating a composition that is capable of inactivating skin-irritating fecal enzymes.

Other objects of the invention will become apparent from the description of the invention which follows.

DETAILED DESCRIPTION OF THE INVENTION AND PREFERRED EMBODIMENTS

According to the method of the invention the irritating effects of fecal proteolytic enzymes are alleviated by contacting the enzymes with materials that inactivate the enzymes by adsorbing them or rendering them incapable of performing their native proteolytic activity. In particular, it has been found that organophilic clays can adsorb fecal enzymes, thereby preventing them from contacting the skin, and also inactivate such enzymes, thereby rendering them incapable of causing irritation to the skin.

According to the method of the invention feces containing irritating proteolytic enzymes are contacted with an amount of organophilic clay sufficient to reduce the activity of the enzymes and thereby decrease or eliminate their ability to cause irritation to the skin. In order to assure that the organophilic clay comes into contact with the proteolytic enzymes it is disposed in anatomical region likely to be contacted by feces, e.g., by applying it to the skin in those areas generally covered by an infant's diaper or by applying it to the diaper itself or incorporating it into the structure of the diaper.

In a preferred embodiment the organophilic clay is incorporated into a pharmaceutically acceptable skin coating material that is applied to the skin, e.g., of an infant, in the region which is subject to contact with feces. The organophilic clay-containing medium is applied sufficiently frequently, e.g., after each diaper change, and in sufficient amount to maintain an effective amount of the organophilic clay associated with the skin where it can adsorb and deactivate the fecal enzymes.

The amount of organophilic clay applied to the skin is evidently not critical, provided that enough is used to produce a substantial decrease in the irritation caused by the fecal enzymes. Typically, the amount of organophilic clay applied to the skin will be at least 0.25 milligrams per square centimeter The organophilic clay used in the method of the invention is typically applied to the skin in a dermatological composition comprising a suspension of the organophilic clay in a pharmaceutically acceptable vehicle. Suitable vehicles include organic and aqueous liquid vehicles, lotions, creams, emulsions, gels or the like. The organophilic clay can also be applied in finely divided form as a mixture with a dusting powder, e.g., as a mixture with a talcum powder or a finely divided starch powder.

The protective composition also may act as a barrier to prevent the fecal enzymes from coming into contact with the skin. The vehicle may contain emollients to aid in healing irritated skin and dispersants if necessary to keep the organophilic clay in suspension. The vehicle should preferably be inert with respect to the organophilic clay, i.e., it should be devoid of materials that will themselves adsorb to the organophilic clay and thereby deactivate the adsorptive or inactivating properties of the organophilic clay which are the basis for its ability to for proteolytic fecal enzymes. In general, compounds having relatively long hydrocarbon chains, i.e., C-8 and longer, should be excluded from the protective composition because such hydrocarbon chains tend to interact with the organophilic clay and reduce or destroy its adsorptive properties for proteolytic fecal enzymes.

Accordingly, a dermatological composition incorporating the organophilic clay for use in the method of this invention might incorporate from about 3% to about 50% by weight of organophilic clay in a conventional dermatological vehicle. Preferably, the composition comprises from about 3% to about 20% by weight and more preferably from about 5% to about 10% by weight.

Suitable vehicles include hydrophobic vehicles such as petrolatum or mineral oil or mixtures thereof, or hydrophilic vehicles such as aqueous-base creams including emulsions of petrolatum and/or mineral oil in water, aqueous-based media thickened with viscosity-adjusting agents. Suitable thickening agents for aqueous-based vehicles include polyoxyethylenes, e.g., polyethylene glycols and derivatives having a molecular weight from about 3000 to about 20,000; polycarboxylic acids, e.g., polyacrylic acid and salts thereof; cellulose derivatives such as hydroxyethyl cellulose, hydroxypropyl cellulose, hydroxypropyl methylcellulose, methylcellulose, carboxymethylcellulose sodium; and hydrophilic organic polymers such as polyvinyl alcohol), poly(vinylpyrrolidone), poly(acrylic acid) sodium salt, and the like. Natural gums such as xanthan gum, carrageenan, gum tragacanth and the like are also useful as thickeners for aqueous-based vehicles. The thickener may also be a colloidal dispersion of a hydrophilic clay such as naturally occurring montmorillonite, bentonite, beidellite, hectorite, saponite, stevensite, or the like, and their synthetically produced analogs.

The dermatological composition incorporating an organophilic clay should have a viscosity sufficient to permit easy spreading on the skin and yet retain the active ingredient in a generally intact layer over the skin to be protected. Dermatological vehicles are well-known to the skilled practitioner and the selection and formulation of an appropriate vehicle is within the capability of such a practitioner without undue experimentation.

The organophilic clay that comprises the barrier and/or fecal enzyme adsorbing and inactivating material in the protective compositions used in the method of this invention may be any conventional organophilic clay of commerce suitable for drug use. Such organophilic clays are well known and can be prepared from any of the clays of the smectite class that are known to swell in water and/or hydrophilic solvents to form viscous suspensions. Suitable clays include naturally occurring montmorillonite, bentonite, beidellite, hectorite, saponite and stevensite, and their synthetically made counterparts. These clays have a lamellar structure wherein alkali metal ions are distributed between the lamellae. Treatment of the clay with long-chain organic amphiphilic compounds such as long-chain quaternary amines results in exchange of the alkali metal ions by cationic organic molecules and thereby renders the clay organophilic.

The quaternary ammonium compounds used in preparing the organophilic clay component of the skin-protecting composition used in the method of the invention typically have one or two long-chain substituents, e.g., 14–20 carbon atom, and two or three short-chain substituents such as methyl groups. A preferred quaternary ammonium compound is dimethyl dihydrogenated tallow ammonium chloride. Because the tallow contains a large proportion of stearic acid, which contains 18 carbon atoms, the resulting clay is often referred to as a quaternium 18 clay, e.g., quaternium 18 bentonite, or quaternium 18 hectorite. The composition and preparation of such organophilic clays is discussed in U.S. Pat. No. 4,861,584. A preferred organophilic clay for use in the method of this invention is quaternium 18 bentonite.

The organophilic clay used in the method of this invention is preferably activated by thorough dispersion with a solvent such as propylene carbonate which is known to increase the adsorptive capability of the clay for organic materials.

The organophilic clay used in the method of the invention can also be incorporated into a garment, such as a diaper, that may come into contact with feces. Fecal enzymes coming into contact with the organophilic clay on the diaper will be inactivated and consequently unavailable to cause irritation to the skin adjacent to the garment. The organophilic clays can be incorporated into a garment such as a diaper by applying them as a coating on the fibers of the garment or as a coating on the web after the garment is fabricated. The garment can also be impregnated with the organophilic clay, either by dipping in a liquid vehicle in which the organophilic clay is suspended and subsequently removing the vehicle, e.g., by evaporation, or by dusting the garment with the organophilic clay alone or in mixture with a dusting powder vehicle, such as described above.

In a preferred embodiment of a fabric according to the invention which can be made into a garment such as a diaper, an organophilic clay may be incorporated into a superabsorbent polymer and the composition so prepared can be incorporated into a fabric, e.g., a non-woven fabric, by procedures conventionally used to incorporate superabsorbent polymers into such fabrics. Such superabsorbent polymers are well known and comprise, among others, cross-linked polymers of acrylic acid, carboxymethyl cellulose cross-linked with epichlorohydrin, poly amino acids, such as polyaspartic acid, cross-linked with, e.g., lysine, graft polymers of cellulose, e.g., wood pulp, and carboxylic monomers, and the like. The preparation of such superabsorbent monomers is conventional and is generally accomplished by polymerizing the monomers in aqueous solution or suspension in an organic solvent in the presence of a suitable initiator of free-radical polymerization. The organophilic clay can be combined with such a superabsorbent polymer by any means that assures adequate dispersal in the polymer matrix. For example, an organophilic clay, e.g., quaternium 18 bentonite, can be dispersed as a finely divided suspension in an aqueous suspension of a superabsorbent polymer such as arises in the manufacture of such polymers by polymerization of conventional hydrophilic monomers in aqueous solution or suspension. This dispersion can be accomplished by conventional high-shear mixing. A solid powder containing the organophilic clay dispersed in the superabsorbent polymer can then be prepared by conventional drying procedures such as spray drying, jet drying, or the like. The superabsorbent polymer containing an organophilic clay can be incorporated into fabric suitable for use in absorbent garments such as diapers and the like by conventional procedures. For example the superabsorbent polymer can be coated onto the woven or non-woven fabric or the fibers thereof, it can be incorporated into pockets in the fabric or between layers of woven or non-woven fabric to form a composite fabric. The superabsorbent polymer can be incorporated into a fabric web by impregnating the web with a solution or suspension of the polymer in water or other suitable vehicle followed by drying the impregnated web. The superabsorbent polymer containing an organophilic clay may also be incorporated into a foam layer, e.g., a polyurethane foam layer which is then fixed to a fabric layer or placed between fabric layers to form a fabric suitable for use in a garment such as a diaper. The superabsorbent polymer containing an organophilic clay can also be incorporated into a non-woven fabric by suspending the polymer in finely divided form in a suspension of the precursor fibers, and then forming the non-woven web by a conventional wet-laying method. Diapers made from fabric containing organophilic clay, when worn by infants, can help to prevent skin irritation caused by fecal enzymes.

EXAMPLE

This example illustrates the effectiveness of quaternium-18 bentonite as an adsorbent and deactivator of fecal proteolytic enzymes.

Tests were conducted on solutions of three proteolytic digestive enzymes, chymotrypsin, trypsin and elastase, to demonstrate the effectiveness of a bentonite clay rendered organophilic by treatment with quaternium 18 (hereinafter referred to as "quaternium 18 bentonite" and "Q-18B") in adsorbing and/or deactivating these enzymes. The amount of enzyme immobilized by adsorption onto the Q-18B was determined by high pressure liquid chromatography (HPLC), and the denaturing effect of the Q-18B was determined by measuring the loss of enzyme activity in standard activity tests and comparing the loss in activity with the loss of activity due to sequestration of the enzyme by adsorption.

In order to conduct the tests determining the adsorption and inactivating effectiveness of Q-18B, aqueous solutions of chymotrypsin, trypsin and elastase were prepared in a phosphate buffer at pH 8, a pH at which these enzymes have been shown to have maximum proteolytic activity. The test solutions contained 0.4 milligrams per milliliter (mg/ml) of chymotrypsin, 0.2 mg/ml of trypsin and 1.0 mg/ml of elastase, respectively. These respective concentrations represent the average infant fecal concentrations of these three principal fecal proteolytic enzymes.

The total amount of enzymatic activity in each solution was measured using 1.0 ml aliquots of each solution, using triplicate experiments and taking an average of the three measured values.

The adsorptive and inactivating effect of Q-18B on each of the enzymes in solution was determined by the following procedure. Test samples comprising 10.0 ml of the enzyme solutions were prepared for each enzyme. To each test sample was added 1.0 gram of Q-18B, and the mixture was mixed with a magnetic stirrer for 10 minutes a low speed. The mixture was then filtered through a prewashed No.1 filter paper and the filtrate was collected and its volume measured carefully. A corresponding control sample was prepared by filtering 10 ml of the enzyme solution through a filter paper. The filtrate was then transferred to a dialysis tube having a dialysis cutoff of 2000 daltons, and dialysis was carried out for 4 hours at 4°–6° C. against deionized water. The retentate from the dialysis step was lyophilized to yield a residual enzyme powder. A known weight of the recovered enzyme was dissolved in a phosphate buffer at pH 8 and the enzyme activity was determined as described above. Because the test procedure itself caused some loss of enzyme and of enzymatic activity, a control was run by dissolving another aliquot of the lyophilized recovered enzyme in an appropriate mobile phase and measuring the amount of enzyme by high pressure liquid chromatography (HPLC). The adsorption and inactivating effect of the Q-18B were assessed by comparing the loss in enzyme and enzymatic activity of the treated test samples with the loss observed for the control samples.

The details of the analytical procedures and the results obtained are described below.

In order to prepare samples for analysis of amount of protein and enzyme activity, the lyophilized retentate was dissolved in 6.0 ml of water and divided into trio 3.0 ml portions. These solutions were again lyophilized to yield solid residues. Thus each experimental determination gave two residues of equal weight which could be used for determining the amount of protein and the enzymatic activity of the enzyme remaining in the enzyme solutions after treatment with Q-18B.

Determination of Amount of Enzyme as Protein:

Chymotrypsin:

A standard chymotrypsin solution was prepared by dissolving 2.30 mg of chymotrypsin in 2.30 ml of water to give a solution having an enzyme concentration of 1.0 mg/ml. An amount of 50 microliters ($\mu$l) of this solution was injected into a high performance liquid chromatograph using a Progel TSK Butyl-NPR column with gradient elution using a mobile phase having an initial composition of 2.3M ammonium sulfate in a pH 8 phosphate buffer and a final composition of plain phosphate buffer, with a gradient time of 10 minutes. The retention time was determined to be 6.1–6.2 minutes.

The lyophilized residues of the control and test samples were each dissolved in 2.0 ml of water, and each of the solutions was filtered through a ball of prewashed cotton and subjected to HPLC using the above protocol. The results of the determinations are summarized in Table 1 below.

Trypsin:

A standard trypsin solution was prepared by dissolving 2.50 mg of trypsin in 2.50 ml of water to give a solution having an enzyme concentration of 1.0 mg/ml. An amount of 50 microliters ($\mu$l) of this solution was injected into a high performance liquid chromatograph using a Progel TSK Butyl-NPR column with gradient elution using a mobile phase having an initial composition of 2M ammonium sulfate in a Tris HCl buffer, pH 7.5, and a final composition of plain buffer devoid of ammonium sulfate, with a gradient time of 10 minutes. The retention time was determined to be 6.61 minutes for beta-trypsin and 7.72 minutes for alpha-trypsin.

The lyophilized residues of the control and test samples were each dissolved in 2.0 ml of water, and each of the solutions was filtered through a ball of prewashed cotton and subjected to HPLC using the above protocol. The results of the determinations are summarized in Table 1 below, wherein the total concentration of trypsin (alpha- and beta-) is given.

Elastase:

A standard elastase solution was prepared by dissolving 1.90 mg of elastase in 0.95 ml of water to give a solution having an enzyme concentration of 2.0 mg/ml. An amount of 50 microliters (μl) of this solution was injected into a high performance liquid chromatograph using a Progel TSK Butyl-NPR column with gradient elution using a mobile phase having an initial composition of 2M ammonium sulfate in a Tris HCl buffer, pH 7.5, and a final composition of plain buffer devoid of ammonium sulfate, with a gradient time of 10 minutes. The retention time was determined to be 7.75 minutes.

The lyophilized residues of the control and test samples were each dissolved in 2.0 ml of water, and each of the solutions was filtered through a ball of prewashed cotton and subjected to HPLC using the above protocol. The results of the determinations are summarized in Table 1 below

TABLE 1

Loss of Enzyme Protein from Solution by Treatment with Q-18B

| | | Control | | Test sample | |
|---|---|---|---|---|---|
| Enzyme | Theoretical amount (mg) | Amount recovered (mg) | Percent loss | Amount recovered (mg) | Percent loss |
| Chymotrypsin | 2.0 | 1.54047 | 22.98 | 0.25687 | 87.16 |
| Trypsin | 1.0 | 1.10293 | 0 | undetectable | 90 |
| Elastase | 5.0 | 0.8867 | 82.23 | 0.38767 | 92.25 |

Determination of Enzyme Activity:

Chymotrypsin:

A standard chymotrypsin solution was prepared by dissolving 0.40 mg of chymotrypsin in 5.0 ml of phosphate buffer. The enzyme concentration was analyzed by the following protocol:

Reagents were prepared as follows:

Reagent A: 80 mM Tris HCl buffer, pH 7.8 at 25° C.;

Reagent B: 1.18 mM sodium benzoyl tyrosine ethyl ester solution; prepared by initially dissolving the reagent in 31.7 ml of methanol and diluting to a volume of 50 ml with deionized water;

Reagent C: 1 mM hydrochloric acid solution;

Reagent D: phosphate buffer (The chymotrypsin enzyme solution was used at a concentration of 2–5 units/ml in reagent D.)

A reaction solution was prepared by mixing 1.42 ml of Reagent A, 1.40 ml of Reagent B, and 0.08 ml of Reagent C. The solution was mixed by inversion and the optical absorbance at a wavelength of 256 nm ($A_{256nm}$) was monitored until it was constant. Thereupon 0.1 ml of the enzyme solution in Reagent D was added to the reaction solution, the solutions were mixed by inversion and the $A_{256nm}$ was monitored for approximately 5 minutes. The maximum rate of increase of optical absorbance ($\Delta A_{256nm}$/min) was taken as the measure of enzyme concentration. A blank was run using only Reagent D without enzyme and the $\Delta A_{256nm}$/min for the blank was subtracted from that for the enzyme solution to yield a value proportional to the concentration of the enzyme.

Test samples were analyzed by dissolving the lyophilized residue from the divided dialysis retentate, containing a maximum of 2.0 mg of chymotrypsin, in 5.0 ml of Reagent D, and determining the actual concentration of chymotrypsin by the above-described protocol using 0.1 ml of the solution. The results of the testing are presented in Table 2 below.

Trypsin:

A standard trypsin solution was prepared by dissolving 0.40 mg of trypsin in 10.0 ml of phosphate buffer solution (cold). The enzyme concentration was analyzed by the following protocol:

Reagents were prepared as follows:

Reagent E: 67 mM sodium phosphate buffer, pH 7.6 at 25° C.;

Reagent F: 0.25 mM sodium benzoyl L-arginine ethyl ester solution;

Reagent G: trypsin enzyme solution containing 350–700 units/ml in Reagent E.

A reaction solution was prepared by equilibrating 3.00 ml of Reagent E at 25° C. and the optical absorbance at a wavelength of 253 nm ($A_{253nm}$) was monitored until it was constant. Thereupon 0.2 ml of Reagent G was added to the reaction solution, the solutions were mixed by inversion and the $A_{253nm}$ was monitored for approximately 5 minutes. The maximum rate of increase of optical absorbance ($\Delta A_{256nm}$/min) was taken as the measure of enzyme concentration. A blank was run using Reagent G without enzyme and the $\Delta A_{256nm}$/min for the blank was subtracted from that for the enzyme solution to yield a value proportional to the concentration of the enzyme.

Test samples were analyzed by dissolving the lyophilized residue from the divided dialysis retentate, containing a maximum of 1.0 mg of chymotrypsin, in 10.0 ml of Reagent E, and determining the actual concentration of chymotrypsin by the above-described protocol using 0.2 ml of the sample solution. The results of the tests are presented in Table 2 below.

Elastase:

An end-point colorimetric method was used to determine the amount of elastase in the test samples, i.e., the lyophilized residue of the divided dialysis retentate.

Reagents were prepared as follows:

Reagent H: 200 mIM Tris buffer, pH 8.8 at 37°;

Reagent I: elastase-orcein substrate;

Reagent J: elastase enzyme solution containing 25–100 units/ml in Reagent H.

A series of elastase substrate solutions was prepared by dissolving weighed amounts of Reagent I in Reagent H. A quantity of the standard or test solution was then mixed with the substrate solutions as follows:

| Solutions/ reagent | Std.1 | Std.2 | Std.3 | Std.4 | Std. 5 | Std. Blank |
|---|---|---|---|---|---|---|
| Reagent I(mg) | 1.0 | 2.0 | 4.0 | 8.0 | 16.0 | 0.00 |
| Reagent H(ml) | 6.00 | 6.00 | 6.00 | 6.00 | 6.00 | 6.00 |

A standard solution of elastase was prepared by dissolving 12.06 mg of elastase in 2.0 ml of buffer to give a solution having 1.03 mg of elastase per milliliter. A quantity of 0.01 ml of the standard elastase solution was added to the substrate solutions, and the solution was mixed by swirling and incubated for 12–16 hours at 37° C. The optical density at a wavelength of 590 nanometers ($A_{590}$) of the standards was measured and a standard curve was prepared.

Test samples were analyzed by dissolving the lyophilized residue from the divided dialysis retentate, containing a maximum of 5.0 mg (600 units) of elastase, in 2.0 ml of buffer, incubating 0.01 ml of the test solutions with substrate mixture for 20 minutes at 37° C. The $A_{590}$ was measured for the test samples and the standard solution prepared by the above protocol, and the amount of enzyme was calculated. The results of the determination are presented in Table 2 below.

TABLE 2

Loss of Enzyme Protein from Solution by Treatment with Q-18B

| Enzyme | Theoretical amount (units) | Control Amount recovered (units) | Percent loss | Test sample Amount recovered (units) | Percent loss |
|---|---|---|---|---|---|
| Chymo-trypsin | 104 | 47.4 | 54.42 | 6.29 | 93.94 |
| Trypsin | 8060 | 5467 | 32.17 | 782.5 | 90.3 |
| Elastase | 350 | 158.2 | 54.8 | 135.5 | 61.29 |

The data presented in the example illustrate that a substantial fraction of the proteolytic fecal enzymes responsible for the skin irritation of diaper rash and the Like are inactivated by contact with organophilic clays such as quaternium-18 bentonite.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A fabric comprising a woven or non-woven web having incorporated therein an organophilic clay, wherein said organophilic clay is a reaction product of a clay selected from the group consisting of naturally occurring and synthetic montmorillonite, bentonite, beidellite, hectorite, saponite and stevensite with a long chain organic quaternary ammonium compound.

2. The fabric of claim 1 wherein said organophilic clay is dispersed in a water-permeable matrix.

3. The fabric of claim 2 wherein said matrix is a superabsorbent polymer.

4. The fabric of claim 3 wherein said superabsorbent polymer is a cross-linked polymer of an unsaturated carboxylic acid.

5. The fabric of claim 4 wherein said unsaturated carboxylic acid is acrylic acid.

6. The fabric of claim 3 wherein said superabsorbent polymer is a cross-linked polymer of an amino acid.

7. The fabric of claim 6 wherein said amino acid is aspartic acid.

8. The fabric of claim 3 wherein said organophilic clay is present in an amount of about 3% to about 50% by weight.

9. The fabric of claim 3 wherein said organophilic clay is present in an amount of about 3% by weight to about 20% by weight.

10. The fabric of claim 3 wherein said organophilic clay is present in an amount of about 3% by weight to about 10% by weight.

11. The fabric of claim 1 wherein said organophilic clay is activated.

12. The fabric of claim 1 wherein said organophilic clay is a reaction product of bentonite with a long chain organic quaternary ammonium compound.

13. The fabric of claim 12 wherein said organophilic clay is activated.

14. The fabric of claim 12 wherein said organophilic clay is quaternium 18 bentonite.

15. The fabric of claim 14 wherein said quaternium 18 bentonite is activated.

16. A garment made from a fabric comprising a woven or non-woven web having incorporated therein an organophilic clay, wherein said organophilic clay is a reaction product of a clay selected from the group consisting of naturally occurring and synthetic montmorillonite, bentonite, beidellite, hectorite, saponite and stevensite with a long chain organic quaternary ammonium compound.

17. The garment of claim 16 wherein said organophilic clay is dispersed in a water-permeable matrix.

18. The garment of claim 17 wherein said matrix is a superabsorbent polymer.

19. The garment of claim 18 wherein said garment is a diaper.

20. The diaper of claim 19 wherein said superabsorbent polymer is a cross-linked polymer of an unsaturated carboxylic acid.

21. The diaper of claim 20 wherein said unsaturated carboxylic acid is acrylic acid.

22. The diaper of claim 19 wherein said superabsorbent polymer is a cross-linked polymer of an amino acid.

23. The diaper of claim 22 wherein said amino acid is aspartic acid.

24. The diaper of claim 19 wherein said organophilic clay is present in said matrix in an amount of about 3% to about 50% by weight.

25. The diaper of claim 19 wherein said organophilic clay is present in said matrix in an amount of about 3% by weight to about 20% by weight.

26. The diaper of claim 19 wherein said organophilic clay is present in said matrix in an amount of about 3% by weight to about 10% by weight.

27. The diaper of claim 19 wherein said organophilic clay is activated.

28. The diaper of claim 19 wherein said organophilic clay is a reaction product of bentonite with a long chain organic quaternary ammonium compound.

29. The diaper of claim 28 wherein said organophilic clay is activated.

30. The diaper of claim 28 wherein said organophilic clay is quaternium 18 bentonite.

31. The diaper of claim 30 wherein said quaternium 18 bentonite is activated.

* * * * *